United States Patent [19]

Böhner et al.

[11] 4,017,640
[45] Apr. 12, 1977

[54] 1-p-ALKYLPHENYL-1-p-(ALKOXY-PHENYL)-2-NITROALKANES

[75] Inventors: Beat Böhner, Binningen; Dag Dawes, Muttenz; Willy Meyer, Riehen, all of Switzerland

[73] Assignee: Ciba-Geigy Corporation, Ardsley, N.Y.

[22] Filed: Jan. 17, 1975

[21] Appl. No.: 541,982

[30] Foreign Application Priority Data

Jan. 21, 1974 Switzerland .................. 786/74
Dec. 21, 1974 Switzerland .................. 15951/74

[52] U.S. Cl. .................. 424/340; 424/337; 260/609 E; 260/612 R
[51] Int. Cl.² .................. C07C 43/20
[58] Field of Search .............. 260/613, 612, 612 R, 260/613 R; 424/340

[56] References Cited

UNITED STATES PATENTS

| 3,657,357 | 4/1972 | Holan | 260/613 R |
| 3,787,505 | 1/1974 | Metcalf et al. | 260/612 R |
| 3,823,192 | 7/1974 | Holan | 260/613 R |

*Primary Examiner*—Bernard Helfin
*Attorney, Agent, or Firm*—Frederick H. Rabin

[57] ABSTRACT 1,1-Diphenyl-2-nitro-pentane, 1,1-diphenyl-2-nitro-hexane and 1,1-diphenyl-2-nitro-heptane derivatives of the formula

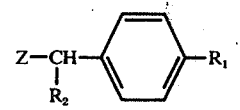

wherein
$R_1$ represents $C_1$–$C_3$-alkyl,
$R_2$ represents p-($C_1$–$C_3$)-alkoxyphenyl or p-($C_1$–$C_3$)-alkylmercaptophenyl,
Z represents

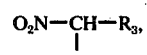

and
$R_3$ represents $C_3$–$C_5$-alkyl, processes for their production and their use in pest control.

9 Claims, No Drawings

1-P-ALKYLPHENYL-1-P-(ALKOXYPHENYL)-2-NITROALKANES

The present invention relates to derivatives of 1,1-diphenyl-2-nitro-pentane, 1,1-diphenyl-2-nitro-hexane and 1,1-diphenyl-2-nitro-heptane, to processes for the production of these derivatives and to their use in pest control.

The said derivatives have the formula

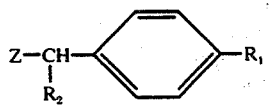

(I)

wherein
$R_1$ represents $C_1$–$C_3$-alkyl,
$R_2$ represents p-($C_1$–$C_3$)-alkoxyphenyl or p-($C_1$–$C_3$)-alkylmercaptophenyl,
Z represents

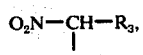

$$O_2N-CH-R_3,$$

and
$R_3$ represents $C_3$–$C_5$-alkyl.

The alkyl, alkoxy or alkylmercaptogroups denoted by $R_1$ to $R_3$ can be branched-chain or straight-chain. These groups are: methyl, methoxy, methylmercapto, ethyl, ethoxy, ethylmercapto, propyl, propoxy, propylmercapto, isopropyl, isopropoxy, isopropylmercapto, n-, i-, sec.-, tert.-butyl or n-pentyl and isomers thereof.

Compounds of formula I preferred on account of their action are those wherein
$R_1$ represent $C_1$–$C_3$-alkyl,
$R_2$ represents p-($C_1$–$C_3$)-alkoxyphenyl,
Z represents

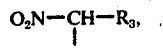

and
$R_3$ represents n-propyl or n-butyl.

The compounds of formula I can be produced, for example, by methods analogous to the following known methods:

a)
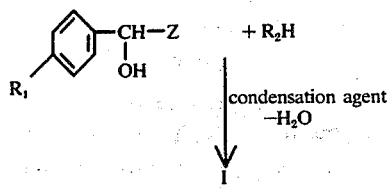

b)
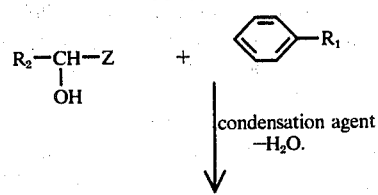

Suitable condensation agents are inorganic acids such as sulphuric acid; organic acids such as acetic acid; Lewis acids such as aluminium chloride or boron trifluoride in the form of complexes with inorganic or organic acids such as phosphoric acid, acetic acid, etc.

The reaction is performed at normal pressure, at a temperature of between −30° and 100° C, preferably between 0° and 40° C, and optionally in solvents, such as acetic acid, nitroalkanes or methylene chloride.

The starting materials of formula II are in some cases known, or they can be produced by methods analogous to known methods, e.g. to those described in the U.S. Pat. No. 2,516,186.

The compounds of formula I have a broad biocidal action and can be used for the control of various plant and animal pests.

Compared with analogous compounds, the compounds of formula I have a surprisingly better insecticidal action, especially against stored-food pests and mosquitoes, a more suitable toxicity with respect to application, and better decomposition properties.

The action of the compounds according to the invention extends in addition to all development stages, such as eggs, larvae, nymphs, pupae and adults, of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae, as well as acarids of the families: Ixodidae, Argasidae and Dermanyssidae.

The insecticidal or acaricidal action can be substantially broadened and adapted to suit the given circumstances by the addition of other insecticides and/or acaricides. Suitable additives are, for example, the following active substances:
organic phosphorus compounds, nitrophenols and derivatives thereof, formamidines, ureas, carbamates and chlorinated hydrocarbons.

The compounds of formula I are advantageously combined also with substances having a synergistic or intensifying action. Examples of such compounds are pyrethrin synergists, such as piperonyl butoxide or Z-(3,4-methylenedioxy-phenoxy)3,6,9-trioxa-undecane (Sesoxane).

The compounds of formula I can be used on their own or together with suitable carriers and/or additives. Suitable carriers and additives may be solid or liquid, and correspond to the substances common in formulation practice, such as natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice. Also to be mentioned are cattle dips and spray races, in which aqueous preparations are used.

The agents according to the invention are produced in a manner known per se by the intimate mixing and/or grinding of active substances of formula I with suitable carriers, optionally with the addition of dispersing agents or solvents which are inert to the active substances. The active substances can be obtained and used in the following forms:

Solid Preparations
 dusts, scattering agents, granulates, coated granulates, impregnated granulates and homogeneous granulates, Liquid Preparations
 a. water-dispersible active-substance concentrates: wettable powders, pastes or emulsions;
 b. solutions.

The content of active substance in the described preparations is between 0.1 and 95%; it is to be mentioned in this connection that in the case of application from an aeroplane, or by means of other suitable devices, concentrations of up to 99.5% can be employed, or even the pure active substance.

The active substances of formula I can be formulated, for example, as follows:

Dusts

The following substances are used in the preparation of (a) a 5% dust, and (b) a 2% dust:

(a)
5 parts of active substance,
95 parts of talcum;

(b)
2 parts of active substance,
1 part of highly dispersed silicic acid,
97 parts of talcum.

The active substances are mixed and ground with the carriers.

Granulate

The following substances are used to produce a 5% granulate:
5 parts of active substance,
0.25 part of epichlorohydrin,
0.25 part of cetyl polyglycol ether,
3.50 parts of polyethylene glycol,
91 parts of kaolin (particle size 0.3 –0.8 mm).

The active substance is mixed with epichlorohydrin and dissolved with 6 parts of acetone; the polyethylene glycol and cetyl polyglycol ether are then added. The solution thus obtained is sprayed on to kaolin, and the acetone is subsequently evaporated off.

Wettable Powder

The following constituents are used in the preparation of (a) a 40%, (b) and (c) a 25%, and (d) a 10% wettable powder:

(a)
40 parts of active substance,
5 parts of sodium lignin sulphonate,
1 part of sodium dibutyl-naphthalene sulphonate,
54 parts of silicic acid;

(b)
25 parts of active substance,
4.5 parts of calcium lignin sulphonate, 1.9 parts of Champagne chalk/hydroxyethyl cellulose mixture (1:1),
1.5 parts of sodium dibutyl naphthalene sulphonate,
19.5 parts of silicic acid
19.5 parts of Champagne chalk,
28.1 parts of kaolin;

(c)
25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr,
46 parts of kaolin;

(d)
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives; the mixture is then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:

(a)
10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

(b)
25 parts of active substance,
2.5 parts of epoxidised vegetable oil,
10 parts of alkylarylsulphonate/fatty alcoholpolyglycol ether mixture,
5 parts of dimethylformamide,
57.5 parts of xylene.

From these concentrates it is possible to prepare, by dilution with water, emulsions of any desired concentration.

Spray

The following constituents are used to prepare a 5% and 95% spray, respectively:
5 parts of active substance,
1 part of epichlorohydrin,
94 parts of ligroin (boiling limits 160°–190° C); and
95 parts of active substance,
5 parts of epichlorohydrin.

EXAMPLE 1

Preparation of
1-p-ethoxyphenyl-1-p-ethylphenyl-2-nitro-n-hexane 25.1 g of 1-p-ethylphenyl-2-nitro-1-hexanol and 14.6 g of ethoxybenzene are dissolved in 80 ml of methylene chloride, and the solution is added dropwise at 0° C, with vigorous stirring, to 90 g of conc. sulphuric acid and 10 ml of water. After 2 hours' stirring at room temperature, the mixture is poured on to 400 ml of ice water. The product is taken up in methylene chloride and washed with saturated sodium bicarbonate solution. After the solvent has been removed by evaporation, the oil remaining behind is dried in high vacuum at 60° C for 2 hours. There is obtained the compound of the formula

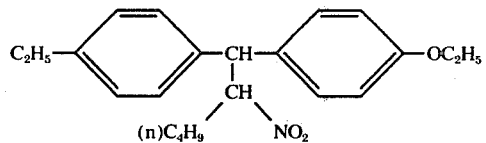

as viscous, dark yellow oil having a refractive index of $n_D^{22} = 1.5452$.

The following compounds can be obtained in an analogous manner:

| R₁ | R₂ | Z | Physical data |
|---|---|---|---|
| —CH₃ | —⟨⟩—OCH₃ | —CH(C₃H₇(n))(NO₂) | $n_D^{20} = 1.5535$ |
| —C₂H₅ | —⟨⟩—OCH₃ | —CH(C₃H₇(n))(NO₂) | $n_D^{20} = 1.5473$ |
| —C₃H₇(n) | —⟨⟩—OCH₃ | —CH(C₃H₇(n))(NO₂) | $n_D^{20} = 1.5360$ |
| —CH₃ | —⟨⟩—OC₂H₅ | —CH(C₃H₇(n))(NO₂) | $n_D^{20} = 1.5475$ |
| —C₂H₅ | —⟨⟩—OC₂H₅ | —CH(C₃H₇(n))(NO₂) | $n_D^{20} = 1.5404$ |
| —C₃H₇(n) | —⟨⟩—OC₂H₅ | —CH(C₃H₇(n))(NO₂) | $n_D^{20} = 1.5309$ |
| —CH₃ | —⟨⟩—OCH₃ | —CH(C₄H₉(n))(NO₂) | $n_D^{20} = 1.5457$ |
| —C₂H₅ | —⟨⟩—OCH₃ | —CH(C₄H₉(n))(NO₂) | $n_D^{20} = 1.5378$ |
| —C₃H₇(n) | —⟨⟩—OCH₃ | —CH(C₄H₉(n))(NO₂) | $n_D^{20} = 1.5375$ |
| —CH₃ | —⟨⟩—OC₂H₅ | —CH(C₄H₉(n))(NO₂) | M.P.: 53 – 55° C |
| —C₃H₇(n) | —⟨⟩—OC₂H₅ | —CH(C₄H₉(n))(NO₂) | $n_D^{20} = 1.5280$ |

-continued

| R₁ | R₂ | Z | Physical data |
|---|---|---|---|
| —C₂H₅ | —⟨⟩—OC₂H₅ | —CH(C₃H₇(i))(NO₂) | |
| —C₂H₅ | —⟨⟩—OC₂H₅ | —CH(C₄H₉(sec))(NO₂) | |
| —C₂H₅ | —⟨⟩—OC₂H₅ | —CH(C₅H₁₁(n))(NO₂) | $n_D^{20} = 1{,}5343$ |

EXAMPLE 2

A. Insecticidal stomach poison action

Cotton and potato plants were sprayed with a 0.1% aqueous active-substance emulsion (obtained from a 10% emulsifiable concentrate).

After the drying of the resulting coating, *Spodoptera littoralis* or *Heliothis virescens* larvae L₃ were placed on to the cotton plants, and Colorado beetle larvae (*Leptinotarsa decemlineata*) on to the potato plants. The test was carried out at 24° C with 60% relative humidity.

Compounds according to Example 1 exhibited in the above test a good insecticidal stomach poison action against *Spodoptera littoralis*, *Heliothis virescens* and *Leptinotarsa decemlineata* larvae.

B. Contact Action Against Adults of *Aëdes aegypti*

With use of an acetonic solution in Petri dishes, 1, 0.1, 0.01 and 0.001 mg of active substance per dish were applied. Each test was performed twice with 10 mosquitoes per concentration. An evaluation was made taking into account both the rate of action and the applied amount to give 100% mortality.

Compounds according to Example 1 exhibited a favourable action in the above test against adults of *Aëdes aegypti*.

EXAMPLE 3

Action Against Ticks

A. *Rhipicephalus bursa*

In each case, 5 adult ticks or 50 tick larvae were placed into a small glass test tube, and subsequently immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

An evaluation in the case of the adults was made after 2 weeks, and in the case of the larvae after 2 days. There were two repeats for each test.

B. *Amblyomma hebraeum*

With a dilution series analogous to that in Test A, tests were carried out using in each case 20 larvae.

Compounds according to Example 1 were effective in these tests against adults and larvae of *Rhipicephalus bursa* and against larvae of *Amblyomma hebraeum*.

We claim:

1. A compound of the formula

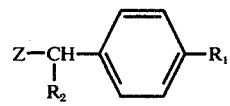

wherein
R₁ represents C₁–C₃-alkyl,
R₂ represents p-(C₁ or C₂)-alkoxyphenyl,
Z represents

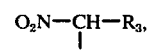

and
R₃ represents C₃–C₅-alkyl.

2. A compound according to claim 1 wherein R₃ represents n-propyl or n-butyl.

3. Compound according to claim 2 of the formula

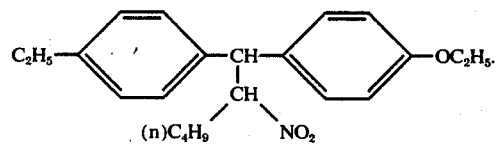

4. Compound according to claim 2 of the formula

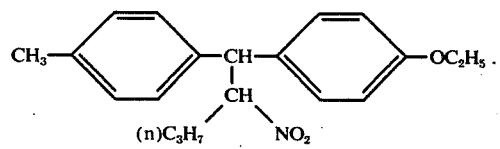

5. A pesticidal composition for controlling insects and acarids which comprises (1) an insecticidally or acaricidally effective amount of a compound according to claim 1 and (2) a carrier.

6. A method for combatting insects and acarids which comprises applying thereto an insecticidally or acaricidally effective amount of a compound according to claim 1.

7. A method according to claim 6 in which $R_3$ represents n-propyl or n-butyl.

8. A method according to claim 7 in which the compound is

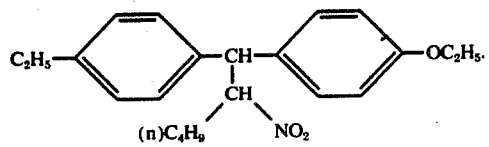

9. A method according to claim 7 in which the compound is

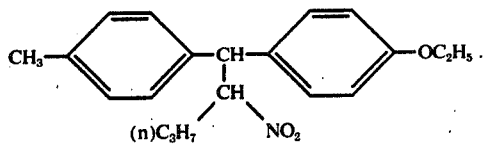

* * * * *